(12) United States Patent
Nishida et al.

(10) Patent No.: US 12,291,727 B2
(45) Date of Patent: May 6, 2025

(54) METHOD FOR PRODUCING STEM CELL-DERIVED LACRIMAL GLAND TISSUE

(71) Applicant: Osaka University, Osaka (JP)

(72) Inventors: Kohji Nishida, Osaka (JP); Ryuhei Hayashi, Osaka (JP); Toru Okubo, Osaka (JP); Yoichi Honma, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 823 days.

(21) Appl. No.: 16/981,455

(22) PCT Filed: Mar. 28, 2019

(86) PCT No.: PCT/JP2019/013759
§ 371 (c)(1),
(2) Date: Sep. 16, 2020

(87) PCT Pub. No.: WO2019/189640
PCT Pub. Date: Oct. 3, 2019

(65) Prior Publication Data
US 2021/0024896 A1   Jan. 28, 2021

(30) Foreign Application Priority Data
Mar. 28, 2018   (JP) ................. 2018-063077

(51) Int. Cl.
*C12N 5/074* (2010.01)
*A61K 35/55* (2015.01)

(52) U.S. Cl.
CPC ............ *C12N 5/0696* (2013.01); *A61K 35/55* (2013.01); *C12N 2501/11* (2013.01); *C12N 2501/15* (2013.01); *C12N 2513/00* (2013.01)

(58) Field of Classification Search
None
See application file for complete search history.

(56) References Cited

U.S. PATENT DOCUMENTS

| | | | | |
|---|---|---|---|---|
| 2013/0280802 A1* | 10/2013 | Schulz | .................. | C12N 5/0606 435/363 |
| 2018/0010093 A1* | 1/2018 | Nishida | ................ | A61K 35/545 |
| 2018/0230425 A1* | 8/2018 | Hirayama | .......... | C07K 14/4702 |
| 2021/0292715 A1* | 9/2021 | Schrepfer | ............ | C12N 5/0696 |

FOREIGN PATENT DOCUMENTS

| WO | WO 2008/045498 A1 | 4/2008 |
|---|---|---|
| WO | WO 2016/114285 A1 | 7/2016 |
| WO | WO 2016/153027 A1 | 9/2016 |
| WO | WO 2017/183655 A1 | 10/2017 |

OTHER PUBLICATIONS

Communication pursuant to Article 94(3 EPC in EP 19775876.6 issue Jun. 13, 2023.
Nagata, Shogo et al., "Induction of Neuroepithelial Cells from Human iPS Cells under Three dimensional Culture using Microfluidic Device" Proceedings of the 42nd Symposium of the Japanese Society of Veterinary Neurology, 2016, pp. 27-28.
International Preliminary Report on Patentability for PCT/JP2009/013759 dated Sep. 29, 2020.
Office Action for CN 201980018449.1 issued Oct. 27, 2022.
Jung, Jae Hun et al., "Proteomic analysis of human lacrimal and tear fluid in dry eye disease" Scientific Reports, Oct. 2017, vol. 7, No. 1.
Supplementary European Search Report for EP 19775876 dated Jun. 2, 2021.
Hayashi, Ryuhei et al., "Co-ordinated ocular development from human iPS cells and recovery of corneal function" Nature, Mar. 2016, pp. 376-380, vol. 531.
Hayashi, Ryuhei et al., "Coordinated generation of multiple ocular-like cell lineages and fabrication of functional corneal epithelial cell sheets from human iPS cells" Nature Protocols, 2017, pp. 683-696, vol. 12, No. 4.
Hirayama, Masatoshi et al., "Identification of transcription factors that promote the differentiation of human pluripotent stem cells into lacrimal gland epithelium-like cells" npj Aging and Mechanisms of Disease, 2017, pp. 1-9, vol. 1.
Kinoshita, Shigeru et al., "Characteristics of the Human Ocular Surface Epithelium" Progress in Retinal and Eye Research, 2011, pp. 639-673, vol. 20, No. 5.
Lu, Qiaozhi et al., "An In Vitro Model for the Ocular Surface and Tear Film System" Scientific Reports, 2017, pp. 1-11, vol. 7, No. 6163.
Ogawa, Miho et al., "Functional salivary gland regeneration by transplantation of a bioengineered organ germ" Nature Communications, 2013, pp. 1-10, vol. 4, No. 2498.
International Search Report for PCT/JP2019/013759 dated Jul. 2, 2019.
Office Action issued in corresponding European patent application No. 19775876.6, dated Feb. 21, 2025, in 6 pages.

* cited by examiner

*Primary Examiner* — Michail A Belyavskyi
(74) *Attorney, Agent, or Firm* — KNOBBE, MARTENS, OLSON & BEAR LLP (57) ABSTRACT

Provided is a method for producing a stem cell-derived lacrimal gland tissue, the method comprising isolating SSEA4 and CD104 double positive cells from a self-formed ectodermal autonomous multi-zone (SEAM) cell population derived from pluripotent stem cells and three-dimensionally culturing the isolated cells in a medium with epidermal growth factor (EGF) and a ROCK inhibitor to produce a cell population expressing a lacrimal gland-related protein. The present invention provides a lacrimal gland organoid produced from pluripotent stem cells including iPS cells and thus is very useful for cell-based regenerative therapy for lacrimal gland-related diseases and cell-based research on the diseases.

6 Claims, 10 Drawing Sheets

METHOD FOR PRODUCING STEM CELL-DERIVED LACRIMAL GLAND TISSUE

CROSS REFERENCE TO RELATED APPLICATIONS

This application is a U.S. National Phase Application of PCT International Application Number PCT/JP2019/013759, filed on Mar. 28, 2019, designating the United States of America and published in the Japanese language, which is an International Application of and claims the benefit of priority to Japanese Patent Application No. 2018-063077, filed on Mar. 28, 2018. The disclosures of the above-referenced applications are hereby expressly incorporated by reference in their entireties.

TECHNICAL FIELD

The present invention relates to a method for producing a stem cell-derived lacrimal gland tissue. In particular, the present invention relates to a method for inducing pluripotent stem cells or limbal stem cells to differentiate into a lacrimal gland tissue and also relates to use of the tissue.

BACKGROUND ART

Human pluripotent stem cells, such as human ES cells and human iPS cells, are receiving worldwide attention for their potential application to regenerative medicine. For practical application of human pluripotent stem cells to regenerative medicine, there is a need to develop techniques for inducing such stem cells to differentiate into somatic cells in a highly efficient and stable manner. To this end, various studies are underway to explore the method for selective differentiation of human pluripotent stem cells into any desired somatic cells.

For example, Non Patent Literature 1 discloses a method for inducing human ES cells to differentiate into lacrimal gland epithelial cells, which method comprises transfecting, into human ES cells, transcription factors (PAX6, SIX1, FOXC1), which are abundant in lacrimal gland epithelial cells.

In addition, the present inventors developed a methodology for fabricating a corneal epithelial cell sheet from iPS cells and examined the efficacy of the cell sheet in an animal model to provide a novel therapy for serious corneal diseases such as limbal stem cell deficiency (see Patent Literature 1 and Non Patent Literature 2 and 3).

CITATION LIST

Patent Literature

Patent Literature 1: WO 2016/114285

Non Patent Literature

Non Patent Literature 1:
Hirayama et al., Npj Aging and Mechanisms of Disease, 3(1), 2017
Non Patent Literature 2:
Hayashi et al., Nature Protocols, 2017, 12(4), 683-696, doi: 10.1038/nprot.2017.007
Non Patent Literature 3:
Hayashi et al., Nature. 2016 Mar 17, 531, 376-80, doi: 10.1038/nature17000

SUMMARY OF INVENTION

Technical Problem

However, even if lacrimal gland epithelial cells can be obtained by induced differentiation according to prior art, there are still hurdles to overcome for application of these cells to regenerative medicine. First, the obtained lacrimal gland epithelial cells need to be able to form a three-dimensional structure consisting of three cell types characteristic of lacrimal gland tissue, namely, ductal cells, acinar cells, and myoepithelial cells. Secondly, the three-dimensional structure needs to become a lacrimal gland tissue capable of secreting lacrimal fluid containing various functional ingredients under the control of the nervous system. These hurdles are not yet overcome.

The present invention relates to a method for producing a stem cell-derived lacrimal gland tissue applicable to regenerative medicine etc., and also relates to use of the tissue.

Solution to Problem

The present inventors have conducted intensive research to solve the above-mentioned problem. As a result, the present inventors have first found that a lacrimal gland-like tissue expressing lacrimal gland-related proteins can be produced in vitro by isolating a specific type of cells by FACS from a multi-zone concentric circular structure (self-formed ectodermal autonomous multi-zone: SEAM) obtained according to the method described in Non Patent Literature 2 and inducing a three-dimensional structure from the isolated cells using Matrigel in the presence of variously combined growth factors.

That is, the present invention relates to the following [1] to [7].

[1] A method for producing a stem cell-derived lacrimal gland tissue, the method comprising
isolating SSEA4 and CD104 double positive cells from a self-formed ectodermal autonomous multi-zone (SEAM) cell population derived from pluripotent stem cells and
three-dimensionally culturing the isolated cells in a medium with epidermal growth factor (EGF) and a ROCK inhibitor to produce a cell population expressing a lacrimal gland-related protein.
[2] The method according to the above [1], wherein the isolated cells are negative for CD200.
[3] A method for producing a stem cell-derived lacrimal gland tissue, the method comprising three-dimensionally culturing limbal stem cells in a medium with epidermal growth factor (EGF) and a ROCK inhibitor to produce a cell population expressing a lacrimal gland-related protein.
[4] The method according to any one of the above [1] to [3], wherein the medium further contains TGF-β.
[5] The method according to any one of the above [1] to [4], wherein the lacrimal gland-related protein is one or more kinds selected from AQP5, LYZ, CNN1, BARX2, SOX9, SOX10, RUNX1, TFCP2L1, LTF, and HTN1.
[6] A method for producing a lacrimal gland organoid for transplantation, the method comprising a step of culturing lacrimal gland epithelial cells obtained by the method according to any one of the above [1] to [5].
[7] A method for drug screening for a lacrimal gland-related disease, the method comprising a step of culturing lacrimal gland epithelial cells obtained by the method according to any one of the above [1] to [5].

The present invention also includes the following [8] and [12].

[8] Lacrimal fluid secreted from a lacrimal gland epithelial cell organoid obtained by the method according to the above [6].
[9] A pharmaceutical composition comprising the lacrimal fluid according to the above [8].
[10] A method for selecting cells that are likely to differentiate into a stem cell-derived lacrimal gland tissue, the method comprising selecting the cells based on cell shape as an indicator from a cell population produced by the method according to any one of the above [1] to [5].
[11] A lacrimal gland organoid obtained by the method according to any one of the above [1] to [6].
[12] A lacrimal gland organoid obtained by culturing cells selected by the method according to the above [10].

Advantageous Effects of Invention

The present invention enables stem cells to differentiate into a lacrimal gland tissue which certainly expresses lacrimal gland-related proteins including functional proteins that the lacrimal gland is supposed to express. Therefore, the lacrimal gland tissue obtained by the present invention is useful to provide a radical regenerative therapy and a next-generation therapy for diseases resulting directly from the abnormality of the lacrimal gland.

In addition, the lacrimal gland tissue obtained by the present invention is applicable to, for example, drug screening using the lacrimal gland as a target organ, which screening has been unfeasible due to limited availability of lacrimal gland cells. Furthermore, the lacrimal fluid secreted from the lacrimal gland tissue obtained by the present invention can be used as an ingredient of a novel drug.

DESCRIPTION OF EMBODIMENTS

The present inventors produced a cell population mimicking the development of a whole eye from iPS cells (self-formed ectodermal autonomous multi-zone: SEAM), isolated a specific type of progenitor cells from the obtained cell population, and subjecting the progenitor cells to induced differentiation, and if needed, maturation culture to produce a high-purity cell population, for example, corneal epithelial cells etc. In the induced differentiation and mature culture of the cells collected from the SEAMS, it is important to use growth factors appropriate for an ultimately desired cell population, but the vessel used is not particularly limited as long as it is a vessel usable for cell culture. In the iPS cell-derived cell population mimicking the eye, each progenitor cell is known to be destined to form a particular region of the eye, but a progenitor cell for lacrimal gland epithelial cells is unknown. To elucidate this matter, the present inventors investigated various ways to induce the progenitor cells obtained as above to differentiate into lacrimal gland epithelial cells. As a result, when three-dimensionally cultured in the presence of specific growth factors, a progenitor cell population known to differentiate into corneal epithelial cells was induced to differentiate into lacrimal gland epithelial cells, resulting in the formation of a lacrimal gland-like tissue expressing lacrimal gland-related proteins including functional proteins comparably with the lacrimal gland in a living body. A similar investigation was performed using a cell population other than that obtained from pluripotent stem cells such as iPS cells. As a result, among some kinds of progenitor cells for corneal epithelial cells, limbal stem cells, which are known to differentiate into corneal epithelial cells in two-dimensional culture, were induced to differentiate into lacrimal gland epithelial cells in the same three-dimensional culture as described above, resulting in the formation of a lacrimal gland-like tissue. The detailed mechanism by which three-dimensional culture induces the differentiation into lacrimal gland epithelial cells is unknown, but a possible hypothesis is that, unlike in the conventional two-dimensional culture, the cells on a three-dimensional scaffold can develop in all the directions while maintaining apicobasal polarity, thus resulting in lacrimal gland epithelial cells, which are able to form three-dimensional structures including a duct and an acinus. However, this hypothesis is not intended to limit the present invention.

The present invention provides a method for inducing differentiation into lacrimal gland epithelial cells, the method comprising three-dimensionally culturing a specific type of progenitor cells separated from SEAMS in the presence of a specific factor. More specifically, the method comprises isolating SSEA4 and CD104 double positive cells from a self-formed ectodermal autonomous multi-zone (SEAM) cell population derived from pluripotent stem cells and three-dimensionally culturing the isolated cells in a medium with epidermal growth factor (EGF) and a ROCK inhibitor to produce a cell population expressing a lacrimal gland-related protein.

The method of the present invention begins with the preparation of a SEAM cell population from pluripotent stem cells.

The pluripotent stem cells used in the present invention are stem cells which have pluripotency, i.e., the ability to differentiate into any type of cells present in a living body, and also have proliferative capacity. Specific examples of the stem cells include embryonic stem cells (ES cells), embryonic stem cells from a cloned embryo obtained by nuclear transfer (ntES cells), spermatogenic stem cells (GS cells), embryonic germ cells (EG cells), induced pluripotent stem cells (iPS cells), and pluripotent cells from cultured fibroblasts or myeloid stem cells (Muse cells). Preferred are ES cells, ntES cells and iPS cells, and more preferred are ES cells and iPS cells. The pluripotent stem cells are preferably pluripotent stem cells of mammals. The mammal is not particularly limited, and examples include humans, mice, rats, cattle, and pigs. Particularly preferred are humans. With the use of human pluripotent stem cells, a desired cell population that is safe and applicable to human regenerative medicine can be obtained.

The SEAM cell population is a colony consisting of multiple concentric circular zones of different ectodermal cells, which colony can be obtained by two-dimensional culture of pluripotent stem cells in a serum-free medium without feeder cells.

More specifically, the SEAM cell population can be obtained by, for example, two-dimensional culture of human iPS cells in a known medium appropriate for animal cell culture (e.g., DMEM medium, BME medium, etc.) without crude or unpurified serum. The culture vessel is not particularly limited as long as it can be used for two-dimensional cell culture. The inner surface of the culture vessel is preferably coated with collagen, fibronectin, laminin or laminin fragment, etc. The culture conditions are not particularly limited and can be appropriately determined according to common technical knowledge.

The SEAM cell population obtained as above is formed as a colony consisting of multiple zones of ectodermal cells generated by cell autonomous differentiation in the absence of exogenous stimuli such as differentiation inducers and differentiation promoters. The colony consists of concentric circular zones of different ectodermal cells, specifically, from the center towards the periphery, the first zone (neuroectodermal lineage cells), the second zone (neural crest lineage cells/optic cup lineage cells), the third zone (ocular surface ectodermal lineage cells), and the fourth zone (surface ectodermal lineage cells). After autonomous differentiation, culture may be continued for further differentiation. This culture can be performed in a medium that is the same as used in autonomous differentiation but is supplemented with various types of growth factors such as ROCK inhibitors and serum replacement, various nutrients required for cell maintenance and growth, and various ingredients required for induced differentiation. These supplements are described later. The method for preparing the SEAMS may be based on any of the methods described in, for example, Non Patent Literature 2 and 3 and Patent Literature 1.

The four zones of the colony contain different lineage cells, and based on this feature, the cells contained in each particular zone may be isolated and used. Alternatively, the whole colony may be used as it is.

The SEAM cell population in the present specification means a cell population obtained by, for example, the following procedure. Pluripotent stem cells are seeded at a density of 100 to 700 cells/cm$^2$ on laminin 511E8 fragment-coated plates, maintained for 8 to 10 days in StemFit (registered trademark) medium (Ajinomoto), and cultured for 4 weeks in a differentiation medium (DM; GMEM (Life Technologies) supplemented with 10% knockout serum replacement (KSR, Life technologies), 1 mM sodium pyruvate (Life Technologies), 0.1 mM non-essential amino acids (Life Technologies), 2 mM L-glutamine (Life Technologies), 1% penicillin-streptomycin solution (Life Technologies) and 55 µM 2-mercaptoethanol (Life Technologies)). After that, culture is continued for 4 weeks in a differentiation medium (CDM; a 1:1 (v/v) mixed medium of DM and Cnt-20 or Cnt-PR (without EGF or FGF2, CeLLnTEC Advanced Cell Systems) supplemented with 10 to 20 ng/mL KGF (Wako), 10 µM Y-27632 (Wako) and 1% penicillin-streptomycin solution), and optionally, the first and second zones are removed. Subsequently, culture is further continued for about 3 days to about 2 weeks in a maintenance medium (CEM; DMEM/F12 (2:1 (v/v)) (Life Technologies) supplemented with 2% B27 supplement (Life Technologies), 1% penicillin-streptomycin solution, 10 to 20 ng/mL KGF and 10 µM Y-27632) for differentiation.

Next, SSEA4 and CD104 double positive cells are isolated from the SEAM cell population obtained above.

In the present invention, the expression of SSEA4 and CD104 is used as an indicator for cell selection. The cell population selected based on these markers is known to differentiate into corneal epithelial progenitor cells, but surprisingly allowed to differentiate into lacrimal gland cells in three-dimensional culture, which is described later.

The isolation method is not particularly limited as long as desired cells can be isolated from the SEAM cell population based on the expression of the two markers as an indicator. The isolation can easily be achieved using antibodies specific for the two markers according to the usual method. More specifically, the isolation can be achieved using antibody-labeled magnetic beads, an antibody-immobilized column, or a cell sorter (FACS) with a fluorescent-labeled antibody. The antibody may be obtained commercially or produced in the usual manner. Before the SSEA4- and CD104-positive selection, CD200 negative selection may be performed in the same manner as for the positive selection. In this case, the isolated cells are CD200−, SSEA4+, and CD104+ cells.

The isolated cells can be directly subjected to three-dimensional culture, but are preferably induced to form spheroids (cell aggregates) prior to three-dimensional culture. In addition, the isolated cells are sorted based on their characteristics prior to spheroid formation.

The isolated cells are the cells selected based on the expression of SSEA4 and CD104 as an indicator, but are likely to include various cells in different states. In order to clarify this matter, the present inventors sorted the isolated cells based on several characteristics and then subjected each cell subset to differentiation culture. As a result, the present inventors found out that the differentiation level varies with cell shape. In the present invention, for example, culturing a specific cell subset separated based on cell shape such as a planar shape (flattened shape) or a solid shape (domed shape) is effective for the control of differentiation into lacrimal gland epithelial cells. Preferably, domed cells are used to form spheroids.

Spheroids can be formed from the isolated cells in culture. The culture medium is not particularly limited as long as it is a known medium appropriate for animal cell culture without crude or unpurified serum. As needed, the culture medium may be supplemented with various types of growth factors, such as ROCK inhibitors, keratinocyte growth factor (KGF), and serum replacement. The culture vessel is preferably one which prevents cells from specific or nonspecific immobilization and allows suspension culture for spheroid formation. For example, low-attachment culture vessels, such as PrimeSurface (registered trademark) 96U plate, can be used. The culture conditions can be appropriately determined according to common technical knowledge.

The culture performed as above allows the isolated cells to form spheroids. The spheroids have a diameter of about 10 to 1000 μm, preferably about 100 to 500 μm. The spheroids have upregulated expression of lacrimal gland epithelial cell-specific markers, such as BARX2, SOX9, and KRT15, and of glandular differentiation markers. Such spheroids are suitable for use in the three-dimensional culture described below.

Three-dimensional culture of the spheroids can be performed according to a known three-dimensional culture method when a medium with EGF and a ROCK inhibitor is used. More specifically, for example, the spheroids are cultured using a biocompatible material, such as hydrogel, laminin, collagen, fibronectin, fibrin, vitronectin, Matrigel (registered trademark), integrin, and glycosaminoglycan, as a cell culture substrate.

The medium used in the three-dimensional culture contains growth factors such as EGF and a ROCK inhibitor to induce lacrimal gland epithelial cell differentiation. The basal medium may be any medium that can be used for epithelial cell culture (serum free medium), and for example, the same one as used in the above-mentioned autonomous differentiation can be used. Serum replacement can also be contained in the medium. The "ROCK inhibitor" as used herein refers to a substance capable of inhibiting Rho kinase (ROCK: Rho-associated, coiled-coil containing protein kinase). Examples of the ROCK inhibitor that can be used include N-(4-pyridinyl)-4β-[(R)-1-aminoethyl]cyclohexane-1α-carboamide (Y-27632), Fasudil (HA1077), (2S)-2-methyl-1-[(4-methyl-5-isoquinolinyl)sulfonyl]hexahydro-1H-1,4-diazepine (H-1152), 4β-[(1R)-1-aminoethyl]-N-(4-pyridyl)benzene-1α-carboamide (Wf-536), N-(1H-pyrrolo[2,3-b]pyridin-4-yl)-4β-[(R)-1-aminoethyl]cyclohexane-1α-carboamide (Y-30141), N-(3-{[2-(4-amino-1,2,5-oxadiazol-3-yl)-1-ethyl-1H-imidazo[4,5-c]pyridin-6-yl]oxy}phenyl)-4-{[2-(4-morpholinyl)ethyl]-oxy}benzamide (GSK269962A), and N-(6-fluoro-1H-indazol-5-yl)-6-methyl-2-oxo-4-[4-(trifluoromethyl)phenyl]-3,4-dihydro-1H-pyridine-5-carboxamide (GSK429286A). Examples of the "serum replacement" include albumin (e.g., lipid-rich albumin), transferrin, fatty acids, collagen precursors, trace elements (e.g., zinc, selenium), B27 (registered trademark) supplement, and N2 supplement. When B27 supplement is used, the concentration of B27 supplement in the medium is 0.01 to 10 wt %, and preferably 0.5 to 4 wt %.

In the present invention, TGF-β can also be contained in the medium to promote cell maturation. TGF-β is not particularly limited and may be TGF-β1, TGF-β2, or TGF-β3. The concentration of TGF-β in the medium is 0.1 to 200 ng/mL, and preferably 1 to 200 ng/mL.

The medium may further contain various nutrients required for cell maintenance and growth and various ingredients required for induced differentiation as needed. Examples of the nutrient include carbon sources such as glycerol, glucose, fructose, saccharose, lactose, honey, starch, and dextrin; hydrocarbons such as fatty acids, fats and oils, lecithin, and alcohols; nitrogen sources such as ammonium sulfate, ammonium nitrate, ammonium chloride, urea, and sodium nitrate; inorganic salts such as sodium chloride, potassium salts, phosphoric salts, magnesium salts, calcium salts, iron salts, and manganese salts (e.g., monopotassium phosphate, dipotassium phosphate, magnesium sulfate, sodium chloride, ferrous sulfate, sodium molybdate, sodium tungstate, and manganese sulfate); various vitamins; and amino acids. The amount of each nutrient can be adjusted according to common technical knowledge.

The culture conditions can be appropriately determined according to common technical knowledge. For example, the culture conditions are 36 to 38° C., preferably 36.5 to 37.5° C., 1 to 25% $O_2$, and 1 to 15% $CO_2$.

The three-dimensional culture performed as above can provide a cell population (lacrimal gland epithelial cells) expressing a protein related to the lacrimal gland. The cell population may be an organoid (lacrimal gland organoid).

In the present invention, the "protein related to the lacrimal gland" encompasses functional proteins that function on the ocular surface after secreted into lacrimal fluid. Specific examples include LTF, LYZ, HTN1, MUC1, MUC4, MUC5AC, MUC5B, MUC6, MUC7, LACRT, and sIgA. LTF is an iron-binding glycoprotein having antimicrobial and antiviral activity. LYZ is a protein that decomposes eubacterial cell walls. HTN1 is a protein having antimicrobial activity and is used as a marker of lacrimal gland epithelial cells. The MUC family is a group of glycoproteins related to water retention on the ocular surface. LACRT contributes to ocular surface cell growth. sIgA plays a key role in mucosal immunity. Preferably, at least one of them is expressed in the cell population.

In the gene analysis, the obtained cell population expresses AQP5, SOX9, SOX10, RUNX1, KRT14, TFCP2L1, CNN1, BARX2, PAX6, etc. in addition to the expression of the above-mentioned functional proteins. In the present invention, these proteins and the above-mentioned functional proteins are collectively referred to as proteins related to the lacrimal gland or lacrimal gland-related proteins. AQP5 is a membrane protein having a pore and one of the representative proteins responsible for water supply for producing lacrimal fluid in acinar cells in the lacrimal gland. SOX9 and SOX10 are transcription factors that play an important role in the development of the lacrimal gland. Both are downstream of signaling from FGF10 and contribute to the development of the lacrimal gland. In particular, SOX10 contributes to acinar cell differentiation. RUNX1 is also known to be a transcription factor that plays an important role in the development of the lacrimal gland. KRT14 is a cytoskeletal protein that is expressed in the lacrimal gland epithelial cells on the basement membrane side during the development of the lacrimal gland. KRT14 is used also as a marker of myoepithelial cells in the mature lacrimal gland. TFCP2L1 is a transcription factor required for differentiation into ductal cells of the lacrimal gland. CNN1 is a protein that is expressed in myoepithelial cells of the lacrimal gland and regulates actomyosin contraction. BARX2 is a transcription factor whose expression is remarkably upregulated during the differentiation process of the lacrimal gland as with KRT15. A direct target of BARX2 is MMP2, which is known to contribute to branching morphogenesis of lacrimal gland tissue, and MMP2 may also be expressed in the obtained cell population. In the present invention, the protein expressed in the obtained cell population is not particularly limited as long as it is a protein related to the lacrimal gland. Such a protein is, for example, one or more proteins selected from AQP5, LYZ, CNN1, BARX2, SOX9, SOX10, RUNX1, TFCP2L1, LTF, and HTN1.

The present invention provides another aspect of the method for inducing differentiation into lacrimal gland epithelial cells, in which limbal stem cells are used in three-dimensional culture. That is, the present invention provides a method for producing a cell population expressing a protein related to the lacrimal gland, the method comprising three-dimensionally culturing limbal stem cells in a medium with EGF and a ROCK inhibitor. Limbal stem cells are already known to differentiate into corneal epithelial cells in two-dimensional culture, but it has newly been found by the present inventors that limbal stem cells differentiate into lacrimal gland epithelial cells in three-dimensional culture. During the induced differentiation of limbal stem cells into lacrimal gland epithelial cells, TGF-β may be contained in the medium to promote cell maturation.

The limbal stem cells may be obtained by induced differentiation of pluripotent stem cells or harvested from a living body. If needed, the obtained or harvested limbal stem cells may be subjected to purification or the like before use. The limbal stem cell population harvested from a living body advantageously has no risk of rejection. The conditions of the three-dimensional culture are the same as those described above except for using limbal stem cells.

The lacrimal gland epithelial cells obtained by the production method of the present invention can be used per se for research, regenerative medicine, etc.

More specifically, for example, when an organoid of the lacrimal gland epithelial cells produced by the production method of the present invention is used as it is for transplantation into a living body, the organoid is expected to become a more mature and functional lacrimal gland tissue in the living body. Alternatively, when the organoid is dissociated and administered in the form of a cell suspension, the cells are expected to be engrafted into lacrimal gland tissue and to promote regeneration. Therefore, the present invention includes a method for producing a lacrimal gland epithelial cell organoid for transplantation, which method comprises a step of culturing the lacrimal gland epithelial cells produced by the production method of the present invention. The culture of the lacrimal gland epithelial cells can be performed in the same manner as in the three-dimensional culture described above. In consideration of maturation in the living body after transplantation, the medium used in the three-dimensional culture here may be free of TGF-β.

In addition, the lacrimal gland epithelial cells produced by the production method of the present invention, which have lacrimal gland-related proteins as with the lacrimal gland in a living body, can greatly contribute to, for example, efficacy evaluation of therapeutic agents for lacrimal gland-related diseases, the analysis of pathogenic mechanisms of lacrimal gland-related diseases, etc. Examples of the lacrimal gland-related disease (the disease resulting directly from the abnormality of the lacrimal gland) include dry eye, Sjogren's syndrome, GvHD, and lacrimal gland tumor.

According to the recent findings, for example, the upregulation of the expression of aquaporins (e.g., AQP5) in the lacrimal gland leads to an increased amount of lacrimal fluid. It is also known that the reduction in the amount of lactoferrin (LTF) correlates with dry eye symptoms, and in this view, the upregulation of the expression of lactoferrin or other functional proteins in lacrimal fluid is expected to alleviate dry eye symptoms. This indicates that the lacrimal gland organoid obtained by the present invention is a potential platform to select a drug capable of increasing the expression and activity of the above-mentioned lacrimal gland-related proteins, that is, is suitable for use in the screening for therapeutic agents for dry eye. Therefore, the present invention includes a method for drug screening for a lacrimal gland-related disease, which method comprises a step of culturing the lacrimal gland epithelial cells produced by the production method of the present invention. The culturing step can be performed in the same manner as in the three-dimensional culture used for induced differentiation into lacrimal gland epithelial cells. In consideration of the expression of lacrimal gland-related proteins, the medium used in the three-dimensional culture here may contain TGF-β.

The screening method of the present invention is not particularly limited as long as it comprises the culturing step described above. In an embodiment of the screening method, the expression of a lacrimal gland-related protein-coding gene or the activity of a lacrimal gland-related protein in the lacrimal gland epithelial cells of the present invention obtained by the culturing step described above is used as an indicator, and a substance capable of promoting the expression or activity is determined as a candidate compound for the treatment of a lacrimal gland-related disease. More specifically, the expression level of a lacrimal gland-related protein-coding gene or the activity level of a lacrimal gland-related protein is measured in the lacrimal gland epithelial cells of the present invention in contact with a test substance, and when the expression level or the activity level is higher than that in control cells not in contact with the test substance, the test substance is determined as a candidate compound for the treatment of a lacrimal gland-related disease.

In addition, since the lacrimal gland epithelial cells produced by the production method of the present invention are equivalent to those in a living body and capable of secreting lacrimal fluid, lacrimal fluid secreted from lacrimal gland epithelial cell organoids produced in vitro by the production method of the present invention can be collected and used as an ingredient of a novel drug. Therefore, the present invention also provides a pharmaceutical composition comprising lacrimal fluid obtained from lacrimal gland epithelial cell organoids produced by the production method of the present invention. The pharmaceutical composition is, for example, a lacrimal fluid eye drop, a dry-eye eye drop, an antimicrobial eye drop, an antiviral eye drop, an antiallergic eye drop, an eye drop for corneal therapy, a steroidal anti-inflammatory eye drop, a nonsteroidal anti-inflammatory eye drop, an eyestrain eye drop, a cataract eye drop, a glaucoma eye drop, or the like. The ingredients other than the above-mentioned lacrimal fluid and the preparation method of the pharmaceutical composition can be appropriately determined according to the usual practice.

EXAMPLES

Hereinafter, the present invention will be described in detail with reference to examples which are illustrative only and should not be construed as limiting the invention. Henceforth, "room temperature" refers to 25° C., and culture conditions are 36 to 38° C., 1 to 25% $O_2$, and 1 to 15% $CO_2$.

Example 1

Induced Differentiation into Ocular Surface Stem Cells

For induced differentiation of iPS cells into eye-related cells, the protocol for self-formed ectodermal autonomous multi-zone (SEAM) formation (Hayashi et al. Nature. 2016 Mar. 17; 531(7594):376-80, Hayashi et al., Nature Protocols, 2017, 12(4), 683-696, doi: 10.1038/nprot.2017.007) was used.

The specific procedure was as follows. Human iPS cells (201B7) were seeded at a density of 100 to 700 cells/cm² on laminin 511E8 fragment-coated plates, maintained for 8 to 10 days in StemFit (registered trademark) medium (Ajinomoto), and cultured for 4 weeks in a differentiation medium (DM; GMEM (Life Technologies) supplemented with 10% knockout serum replacement (KSR, Life technologies), 1 mM sodium pyruvate (Life Technologies), 0.1 mM non-essential amino acids (Life Technologies), 2 mM L-glutamine (Life Technologies), 1% penicillin-streptomycin solution (Life Technologies) and 55 µM 2-mercaptoethanol (Life Technologies)). After that, culture was continued for 4 weeks in a differentiation medium (CDM; a 1:1 (v/v) mixed medium of DM and Cnt-20 or Cnt-PR (without EGF or FGF2, CeLLnTEC Advanced Cell Systems) supplemented with 10 to 20 ng/mL KGF (Wako), 10 µM Y-27632 (Wako) and 1% penicillin-streptomycin solution) and subsequently for additional about 2 weeks in a maintenance medium (CEM; DMEM/F12 (2:1 (v/v)) (Life Technologies) supplemented with 2% B27 supplement (Life Technologies), 1% penicillin-streptomycin solution, 10 to 20 ng/mL KGF and 10 µM Y-27632) for SEAM induction.

After 6 weeks of SEAM induction, the wells were washed with PBS, and fixation was performed with 4% PFA at room temperature for 30 minutes. After blocking with 5% NST (TBS supplemented with 5% normal donkey serum and 3% Triton), the SEAMS were permeabilized with 1% NST (TBS supplemented with 1% normal donkey serum and 3% Triton) for 3 days. Afterwards, the SEAMS were subjected to primary antibody reaction using an anti-PAX6 antibody (sc-53108) or an anti-BARX2 antibody (sc-9128) for 3 days. After washing, the SEAMS were stained with the corresponding secondary antibody labeled with Alexa Fluor 488 or 568 for 1 hour. The nuclei were stained with Hoechst 33342 for the final 10 minutes of the secondary antibody reaction. The results are shown in FIG. 1.

Figure 1:
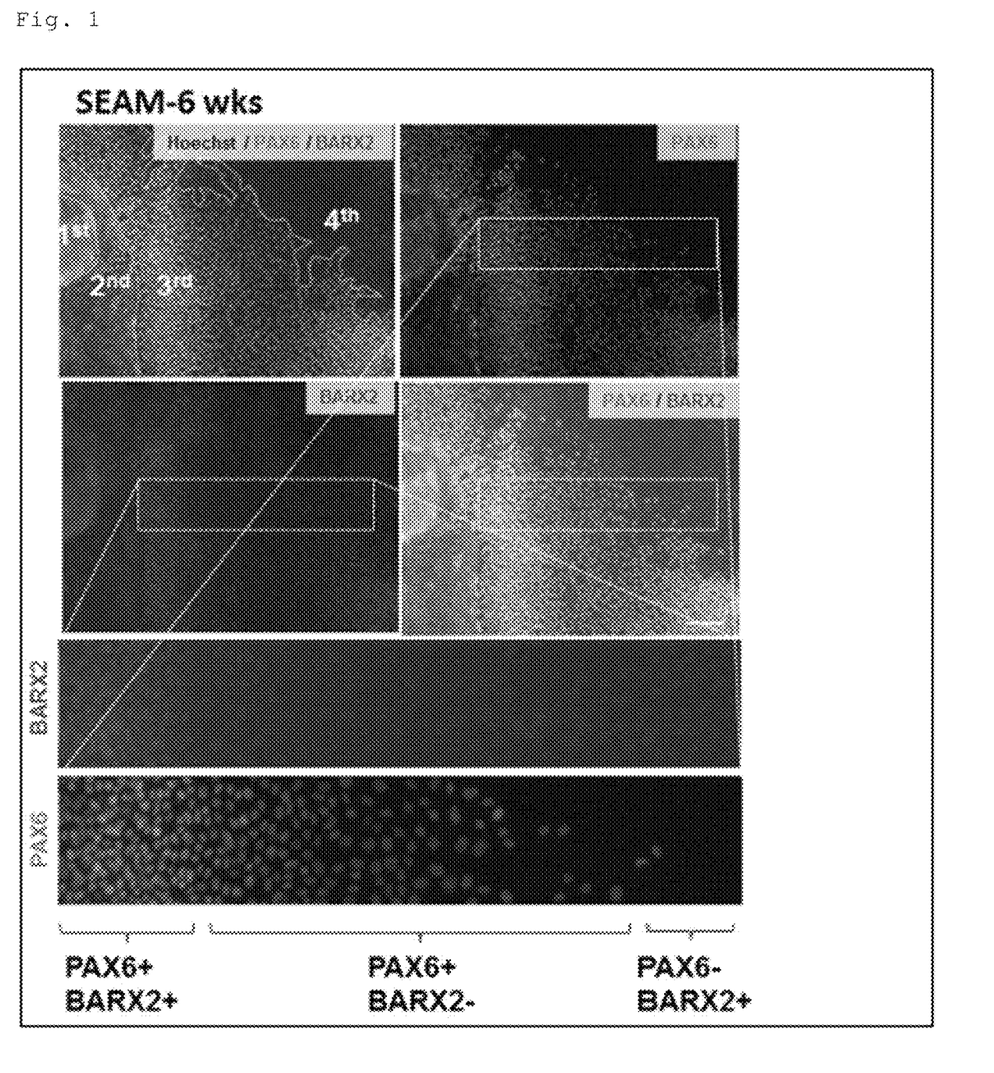
FIG. 1 shows the results of immunofluorescent staining of a two-dimensional tissue structure consisting of four concentric circular zones (SEAM) induced from iPS cells.

As shown in FIG. 1, the SEAMS had a 4-zone structure composed of the first zone (1st in the figure), the second zone (2nd in the figure), the third zone (3rd in the figure), and the fourth zone (4th in the figure). Also shown was that ocular surface stem cells (PAX6/BARX2 double positive cells) were abundant in the third zone, in particular, a region of the third zone near the second zone.

Example 2

Induction of Lacrimal Gland Organoids

CD200−, SSEA4+, and CD104+ ocular surface stem cells were collected from the SEAMS obtained in Example 1.

The obtained ocular surface stem cells were seeded on PrimeSurface (registered trademark) 96U plates (Sumitomo Bakelite Co., Ltd.) at 50,000 cells/spheroid in DMEM/F-12 with B27 supplement containing 10 µM Y-27632 and 20 ng/mL KGF and cultured for 1 day to form spheroids (diameter: about 560 µm). The spheroids were embedded in Matrigel GFR (Corning) and cultured in DMEM/F-12 with B27 supplement containing 10 µM Y-27632, 10 ng/mL EGF, and 100 ng/mL TGF-β3 for 2 weeks. The results are shown in FIG. 2.

Figure 2:
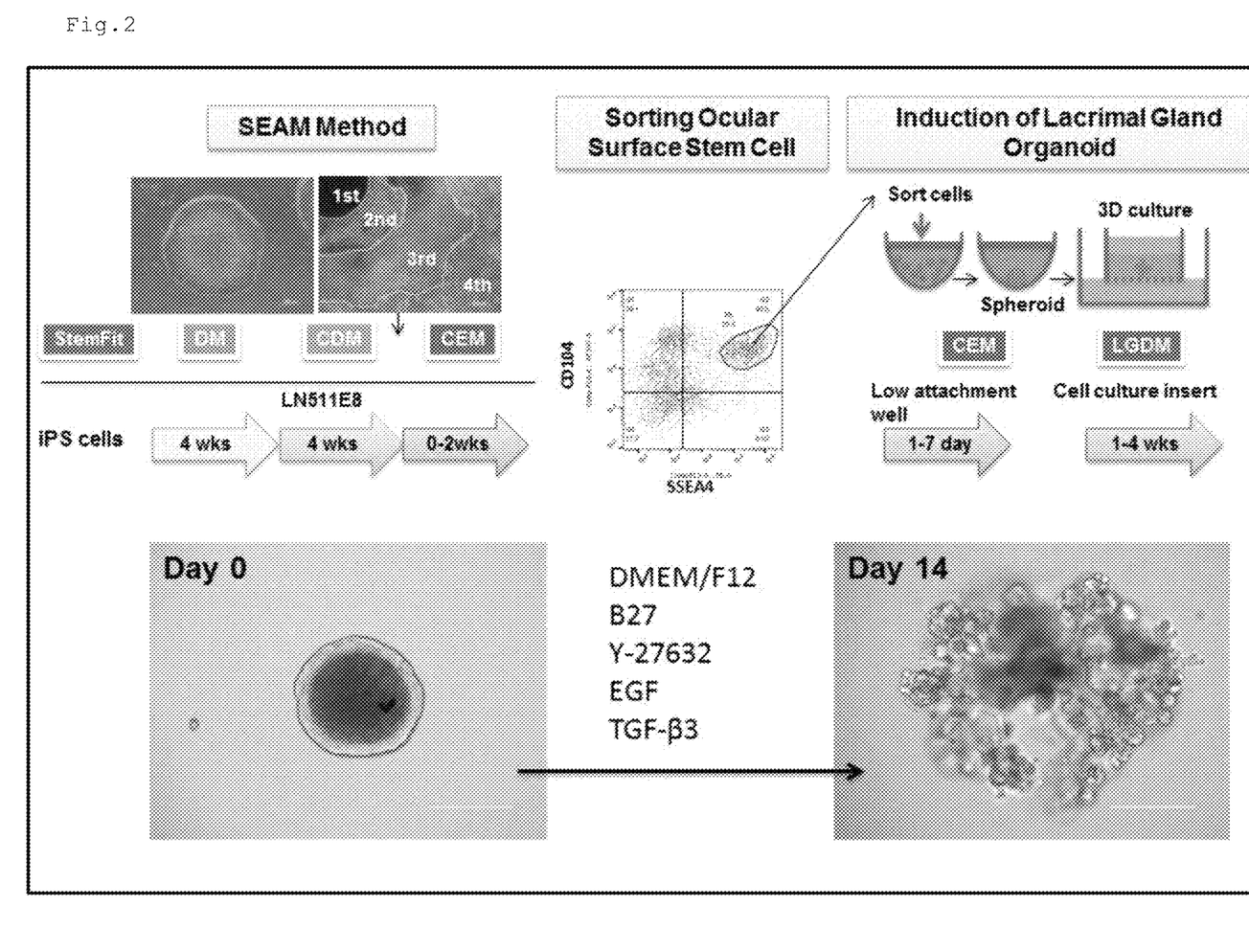
FIG. 2 shows a typical example of the induction process from iPS cells to a lacrimal gland organoid.

FIG. 2 shows that the ocular surface stem cells formed organoids having an adenoid structure.

Example 3

Gene Expression Analysis During Induction of Lacrimal Gland Organoids

For gene expression analysis, the following samples were prepared. The first sample was prepared by 10-day culture of human iPS cells in StemFit as described in Example 1 and is hereinafter referred to as "iPSC". The second sample was prepared by 8- to 10-week SEAM induction as described in Example 1 and subsequent separation of a SSEA4/CD104 double positive fraction and is hereinafter referred to as "Sort". The third sample was prepared by spheroid formation as described in Example 2 and is hereinafter referred to as "Spheroid". The fourth sample was prepared by organoid formation as described in Example 2 and is hereinafter referred to as "Organoid". RNA was collected from each sample using QIAzol Lysis Reagent (QIAGEN) and subjected to qRT-PCR to examine the expression of various markers in each stage. The results are shown in FIG. 3.

Figure 3:
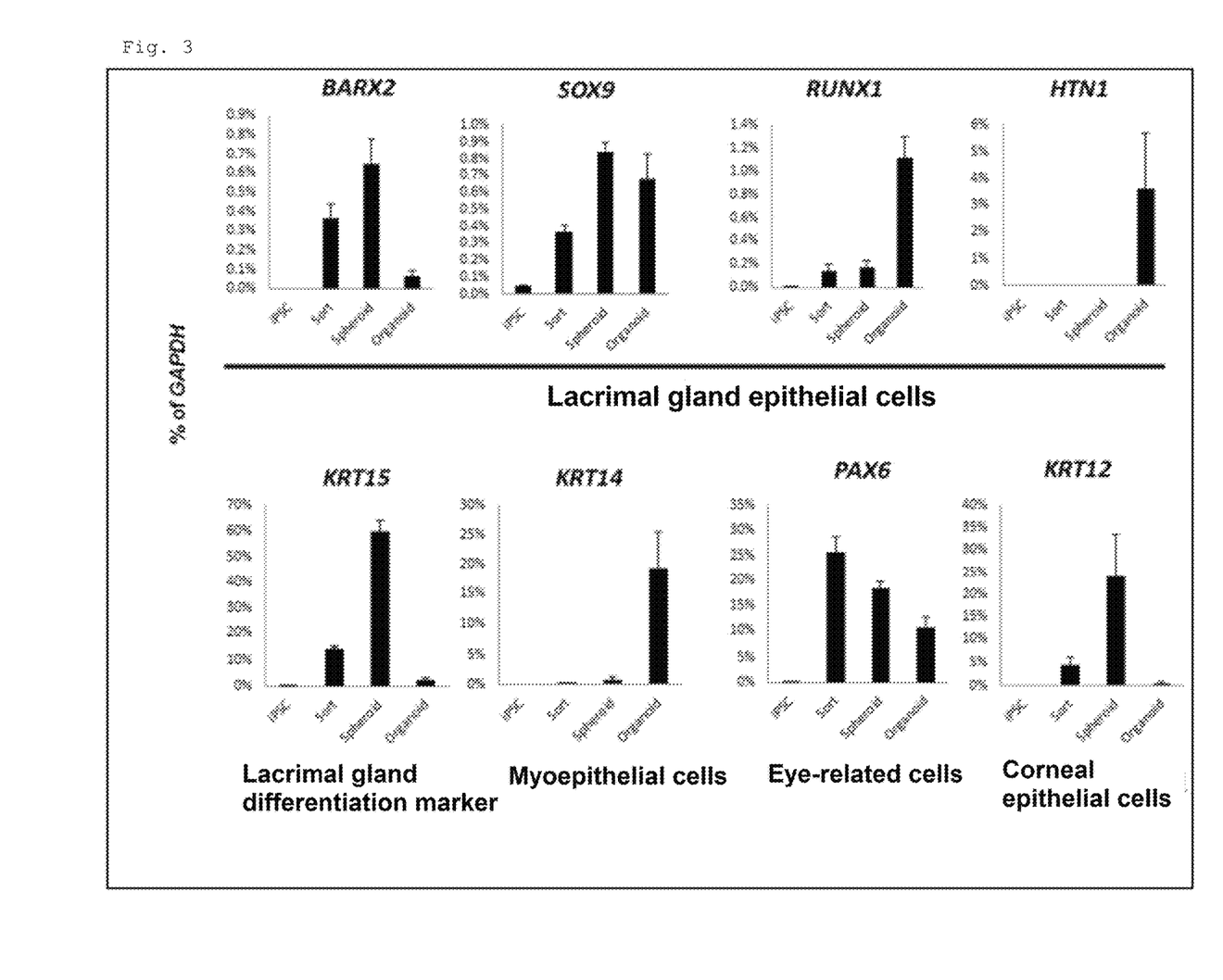
FIG. 3 shows the results of gene expression analysis in iPS cell-derived lacrimal gland organoids.

FIG. 3 shows that Organoid expressed the markers related to lacrimal gland epithelial cells. In particular, BARX2 and KRT15, which are known to be upregulated in the middle stage of differentiation, were highly expressed in Spheroid, and their expression was reduced in the later stage. This indicates that Organoid is in a more advanced state of differentiation as compared with Spheroid. In addition, Organoid retained PAX6 expression and highly expressed SOX9, RUNX1, and a functional protein, HTN1. This indicates that Organoid is a lacrimal gland in a more advanced state of differentiation.

Example 4

Immunofluorescent Staining of Lacrimal Gland Organoids

The cultured lacrimal gland organoids were blocked with 5% NST (TBS supplemented with 5% normal donkey serum and 3% Triton) and subjected to primary antibody reaction using an anti-PAX6 antibody (sc-53108), an anti-HTN1 antibody (sc-28110), or an anti-CAL antibody (ab46794). Separately, the cultured lacrimal gland organoids were fixed with 4% PFA, sliced into sections, and subjected to blocking and primary antibody reaction in the same manner as above. After washing, staining with the corresponding secondary antibody labeled with Alexa Fluor 488 or Alexa Fluor 568 was performed for 1 hour. The nuclei were stained with Hoechst 33342 for the final 10 minutes of the secondary antibody reaction. The results are shown in FIG. 4.

Figure 4:
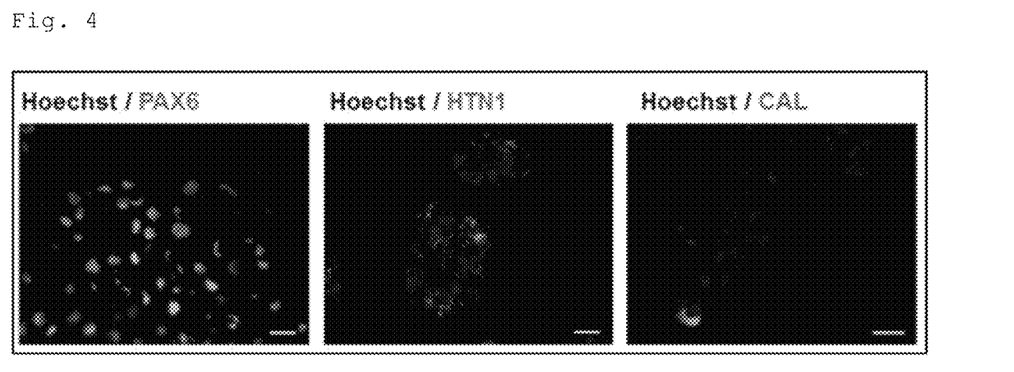
FIG. 4 shows the results of immunofluorescent staining of iPS cell-derived lacrimal gland organoids.

As shown in FIG. 4, the organoids retained PAX6 expression and certainly expressed the functional protein HTN1, the myoepithelial cell marker CAL, etc., which are proteins that can be expressed in lacrimal gland cells.

Example 5

Examination of Conditions for Induction of Lacrimal Gland Organoids (Growth Factor Type)

Three-dimensional culture was performed as described in Example 2 in the presence of 10 ng/mL EGF, 10 ng/mL EGF plus 10 µM Y-27632, or 10 ng/mL EGF plus another growth factor reportedly involved in lacrimal gland differentiation, namely, 20 ng/mL KGF, 100 ng/mL FGF10, or 100 ng/mL BMP7. The results are shown in FIG. 5A.

Similarly, three-dimensional culture was performed in DMEM/F-12 with B27 supplement, 10 ng/mL EGF, and 10 µM Y-27632 containing 100 ng/mL TGF-β1, β2, or β3. The results are shown in FIG. 5B.

Figure 5:
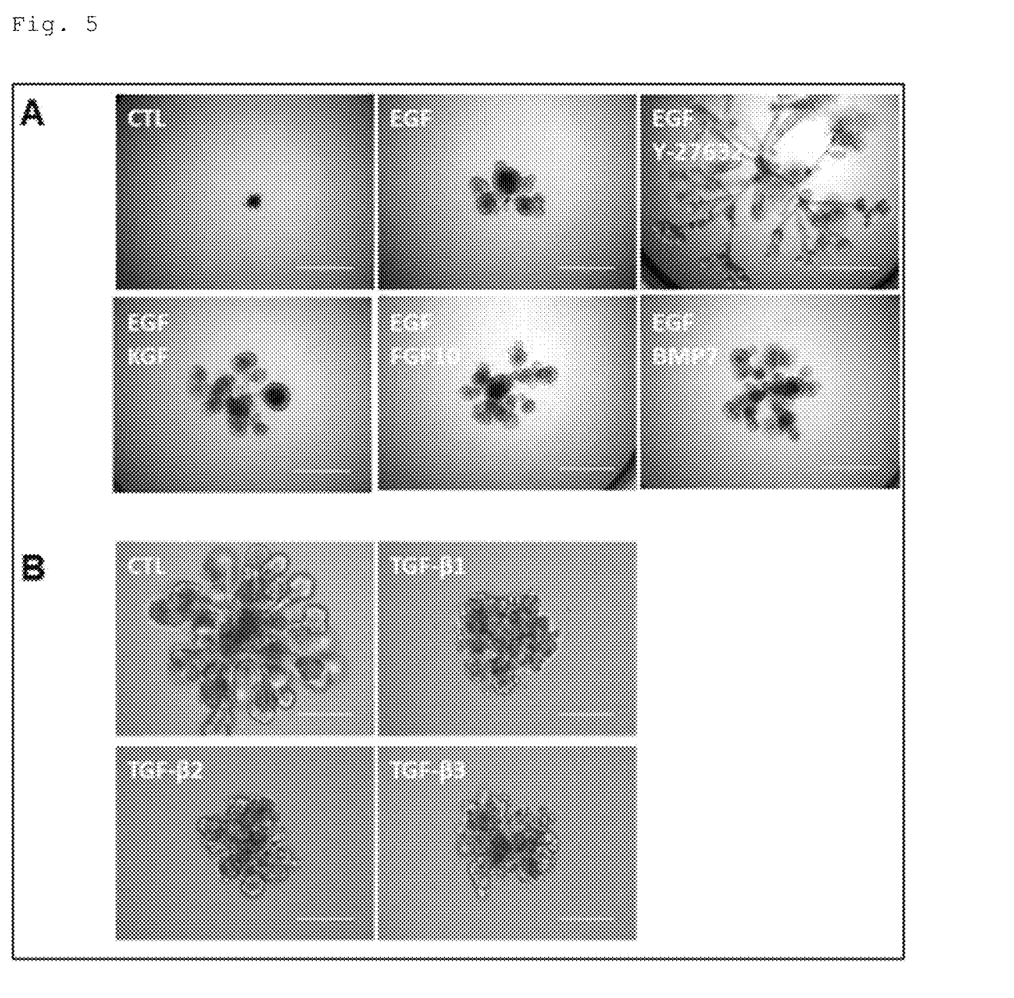
FIG. 5 shows the results of the examination of the conditions for induction of iPS cell-derived lacrimal gland organoids (growth factor type).

As shown in FIG. 5A, KGF, FGF10, and BMP7, which are known to be involved in lacrimal gland differentiation, were less effective in combination with EGF in promoting lacrimal gland differentiation, while 10 ng/mL EGF plus 10 µM Y-27632 remarkably promoted lacrimal gland differentiation. These results indicate that a combination of EGF and Y-27632 is effective. In addition, FIG. 5B shows that TGF-β, regardless of its subtype, helped further maturation of the lacrimal gland structure.

Example 6

Examination of Conditions for Induction of Lacrimal Gland Organoids (TGF-β Concentration)

Three-dimensional culture was performed as described in Example 2 in a medium with 10 ng/mL EGF and 10 µM Y-27632 containing 4, 20, or 100 ng/mL TGF-β3. The results are shown in FIG. 6A.

RNA was collected from each sample using QIAzol Lysis Reagent and subjected to gene expression analysis as described in Example 3. The representative results are shown in FIG. 6B.

Figure 6:
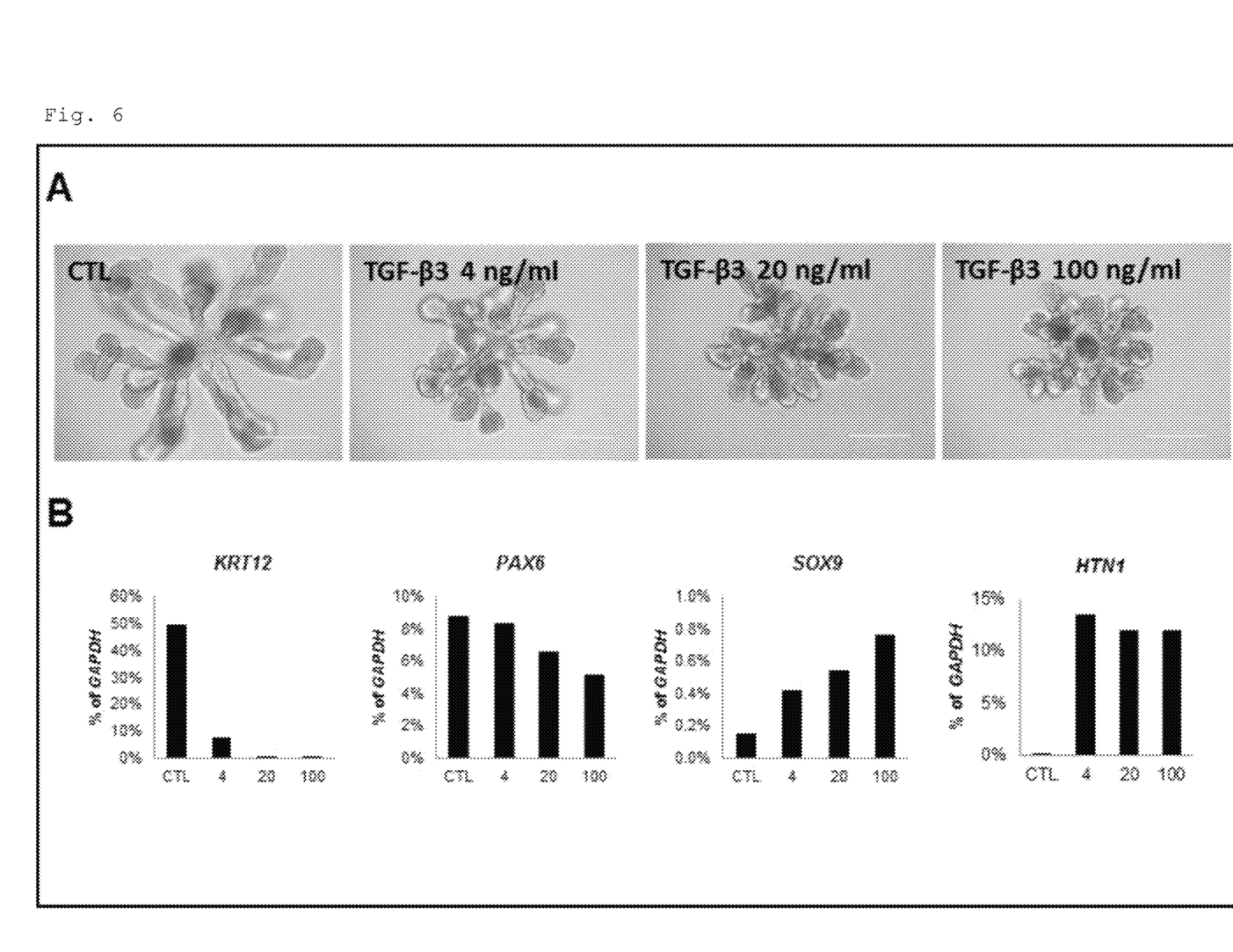
FIG. 6 shows the results of the examination of the conditions for induction of iPS cell-derived lacrimal gland organoids (TGF-β concentration).

As shown in FIGS. 6A and 6B, maturation was promoted to some extent even at as low as 4 ng/mL TGF-β3, and the extent of maturation increased in a TGF-β3 concentration dependent manner.

Example 7

Examination of Conditions for Induction of Lacrimal Gland Organoids (Colony Shape)

Figure 7:
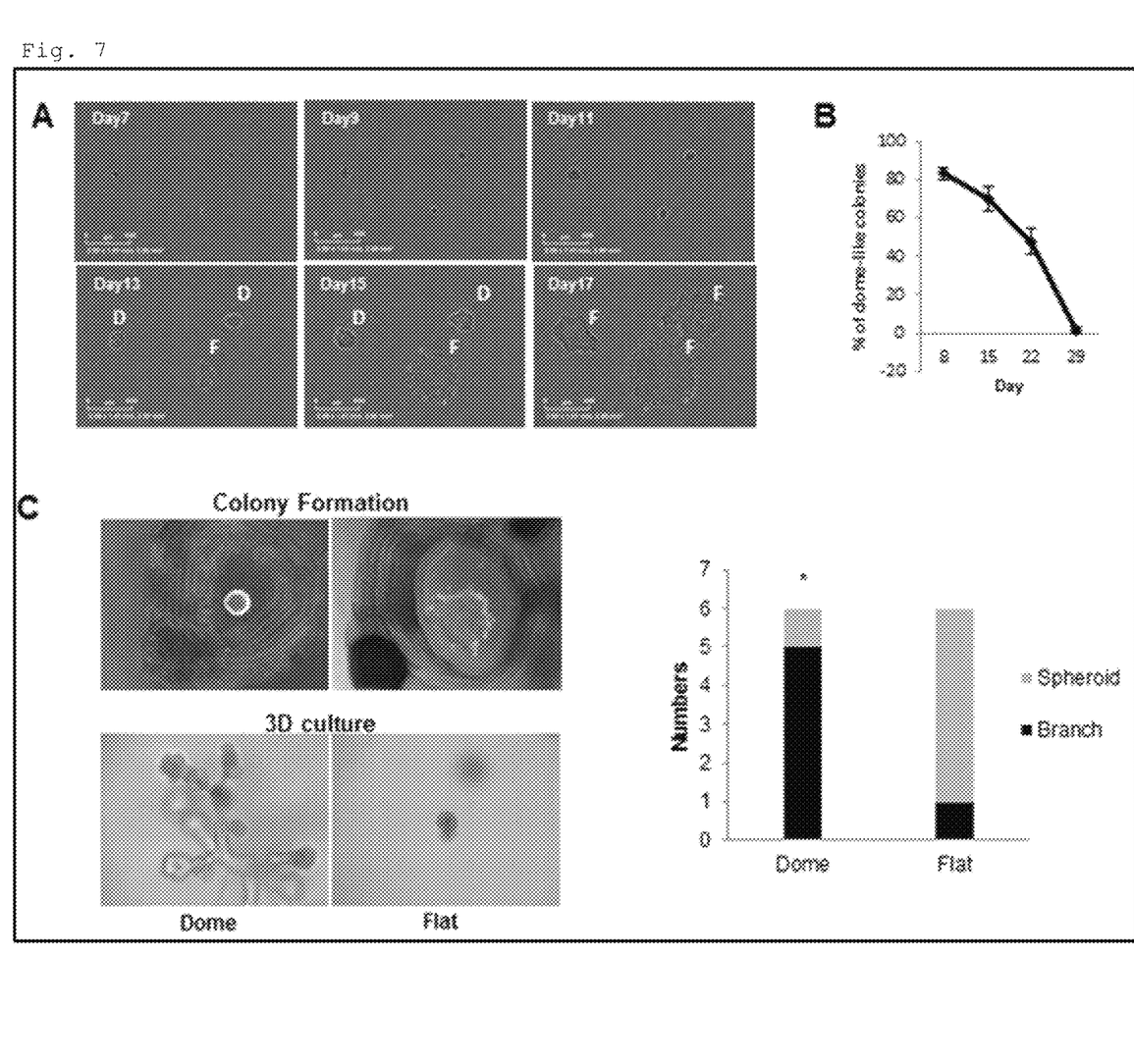
FIG. 7 shows the results of the examination of the conditions for induction of iPS cell-derived lacrimal gland organoids (colony shape).

The CD200−, SSEA4+, and CD104+ ocular surface stem cells collected in Example 2 were seeded at 100 to 200 cells/well (12-well plate) and cultured in DMEM/F-12 with 2% B27 supplement, 20 ng/mL KGF, and 10 µM Y-27632 for 29 days. The progress of colony formation was time-lapse recorded. The results are shown in FIG. 7A.

The colony shape has 2 types (flattened shape: F, domed shape: D). As shown in FIG. 7A, the colony shape gradually was shifted to a flatted one over the culture period (FIG. 7B shows the percentage of the number of domed colonies in the total number of colonies). The colonies of each shape were picked up, embedded in Matrigel GFR (Corning), and three-dimensionally cultured in DMEM/F-12 with B27 supplement containing 10 µM Y-27632 and 10 ng/mL EGF. While the flattened colonies remained spheroidal (Spheroid) and were less likely to form a lacrimal gland-like structure, the domed colonies were highly likely to form a lacrimal gland-like structure (Branch) (FIG. 7C). These results indicate that the domed colonies are more likely to form a lacrimal gland-like structure.

Example 8

Induction of Lacrimal Gland Organoids from Human Limbal Stem Cells

Human limbal stem cells were seeded on iMatrix-511-coated dishes and two-dimensionally cultured in DMEM/F-12 with B27 supplement containing 20 ng/mL KGF and 10 µM Y-27632 for 16 days (Sheet). Separately, from 20,000 cells of human limbal stem cells, spheroids were formed as described in Example 2, embedded in Matrigel GFR, and three-dimensionally cultured in DMEM/F-12 with B27 supplement containing 10 ng/mL EGF and 10 µM Y-27632 (YE) or in DMEM/F-12 with B27 supplement containing 10 ng/mL EGF, 10 µM Y-27632, and 100 ng/mL TGF-β3 (YET3). The results are shown in FIG. 8A.

RNA was collected from each sample using QIAzol Lysis Reagent and subjected to gene expression analysis as described in Example 3. The representative results are shown in FIG. 8B.

Figure 8:
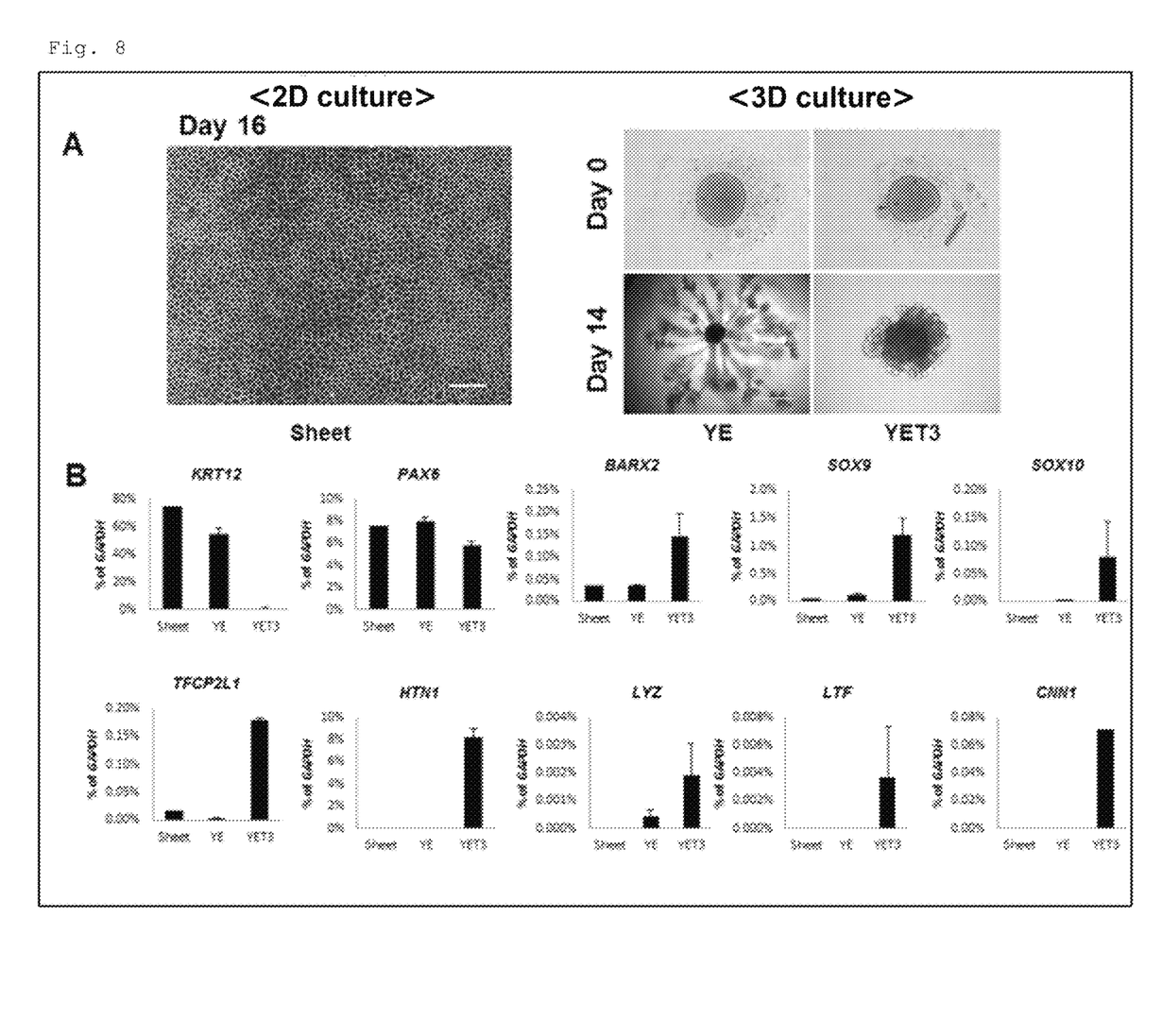
FIG. 8 shows the morphology of limbal stem cell-derived cells and the results of gene expression analysis in the limbal stem cell-derived cells.

As shown in FIGS. 8A and 8B, the human limbal stem cells in two-dimensional culture were induced to form a corneal epithelial cell sheet, while the human limbal stem cells in three-dimensional culture were induced to form organoids having an adenoid structure. In three-dimensional culture, the expression of the markers related to lacrimal gland epithelial cells was upregulated in a stepwise manner from YE to YET3, indicating the promotion of maturation.

Example 9

Experiment of Transplantation into Nude Rat and Transplant Analysis

From a 5-week-old female F344/NJcl-rnu/rnu (nude rat), the left exorbital lacrimal gland was excised, and to this site, a lacrimal gland organoid was transplanted. The lacrimal gland organoid was prepared beforehand by culturing 50,000 cells of iPS cell-derived ocular surface stem cells in DMEM/F-12 with B27 supplement, 10 ng/mL EGF, and 10 µM Y-27632 for 25 days. At 34 days after the transplantation, the rat was euthanized, and the transplant was excised and analyzed (FIGS. 9A, 9B, 9C).

Figure 9:
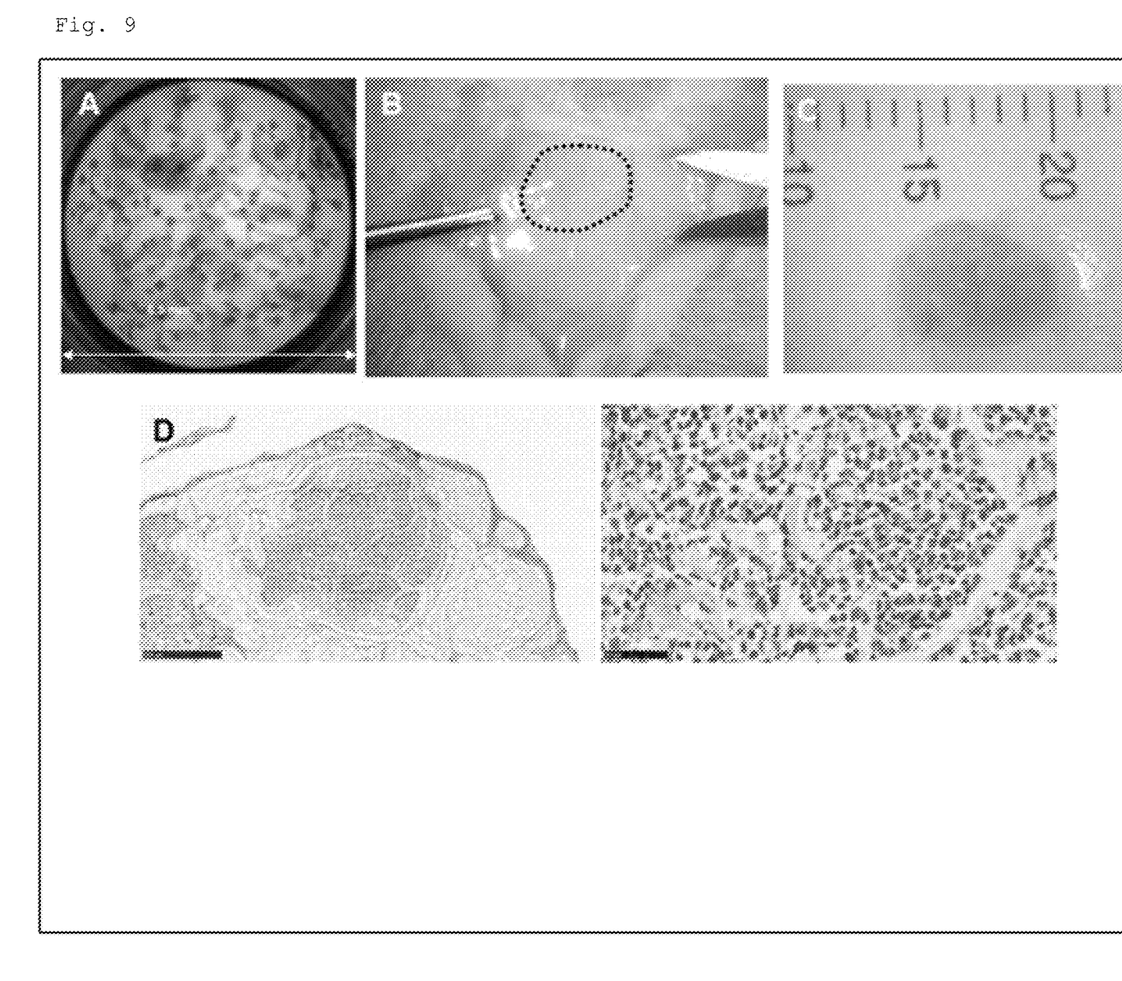
FIG. 9 shows the results of HE staining of the transplant in a nude rat transplanted with an iPS cell-derived lacrimal gland organoid.

The transplant was embedded in OCT compound, fixed with a 10% neutral buffered formalin solution, and subjected to HE-staining (FIG. 9D).

Figure 10:
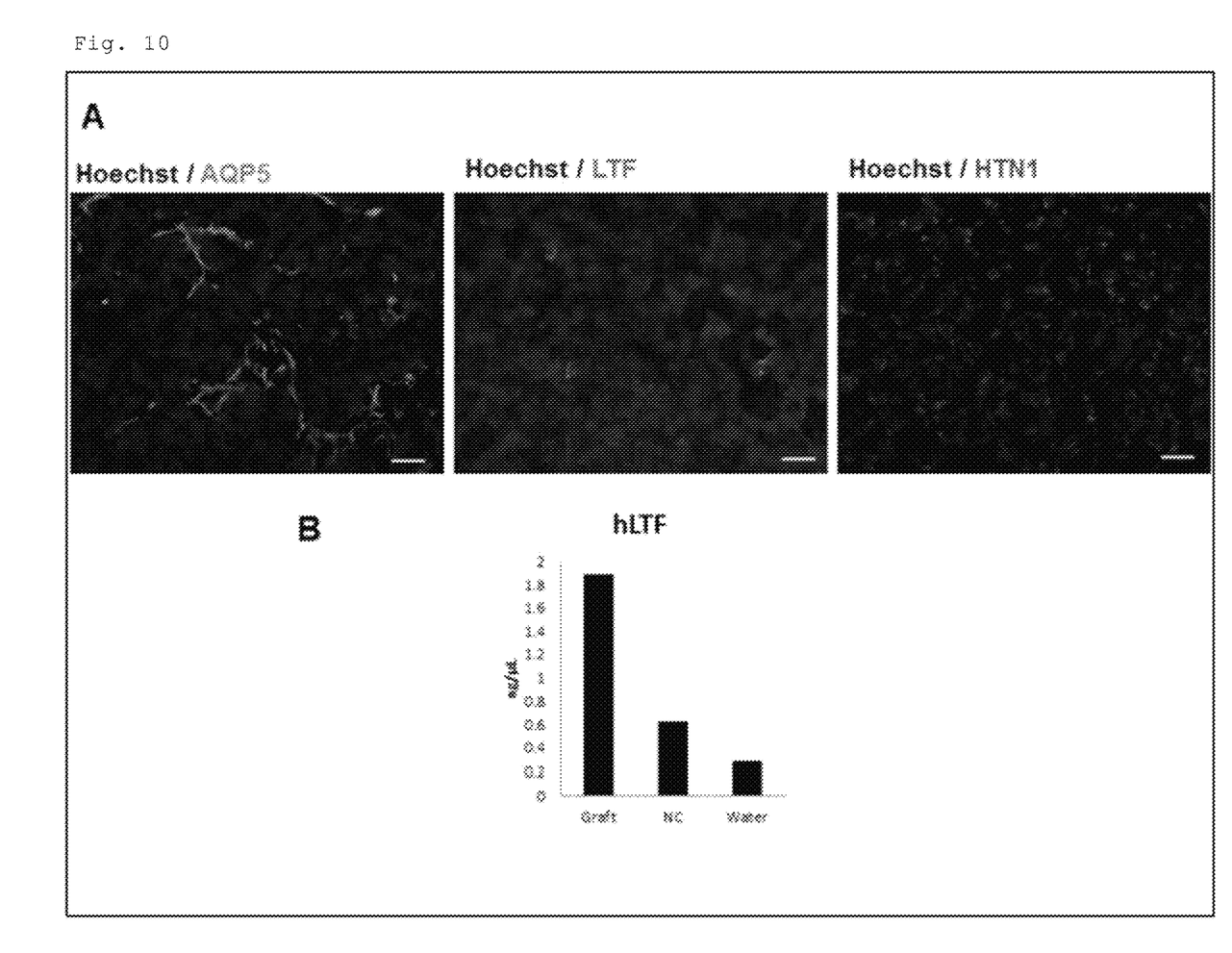
FIG. 10 shows the results of immunofluorescent staining of the transplant in a nude rat transplanted with an iPS cell-derived lacrimal gland organoid and the results of the measurement of the hLTF protein content of the transplant extract.

In addition, the sections of the transplant were blocked with 5% NST (TBS containing 5% normal donkey serum and 3% Triton) and subjected to primary antibody reaction using an anti-AQP5 antibody (sc-9890), an anti-LTF antibody (ab15811), or an anti-HTN1 antibody (sc-28110). After washing, staining with the corresponding secondary antibody labeled with Alexa Fluor 488 or Alexa Fluor 568 was performed for 1 hour. The nuclei were stained with Hoechst 33342 for the final 10 minutes of the secondary antibody reaction (FIG. 10A).

The extract of the transplant was subjected to hLTF ELISA (ab108882) to measure the hLTF protein content of the transplant. For comparison, the nude rat lacrimal gland extract (NC) and water (Water) were used in the same measurement (FIG. 10B).

The iPS cell-derived lacrimal gland organoid expressed the major functional proteins of lacrimal gland tissue even after transplanted, indicating that the iPS cell-derived lacrimal gland organoid has a sufficient potential for application to regenerative medicine.

Example 10

Induction of Lacrimal Gland Organoids from ES Cells

The same procedure as described in Examples 1 and 2 was performed to induce organoids. The specific procedure was as follows. From human ES cells (KhES-1), a SEAM cell population was prepared as described in Example 1. From the SEAM cell population, ocular surface stem cells were collected as described in Example 2. The obtained ocular surface stem cells were seeded on PrimeSurface (registered trademark) 96U plates at 100,000 cells/spheroid in DMEM/F-12 with B27 supplement containing 10 µM Y-27632 and 20 ng/mL KGF and cultured for 1 day to form spheroids. The spheroids were embedded in Matrigel GFR and cultured in DMEM/F-12 with B27 supplement containing 10 µM Y-27632 and 10 ng/mL EGF for 2 weeks. Bright-field images were recorded on day 1, day 3, and day 14. The results are shown in FIG. 11.

Figure 11:
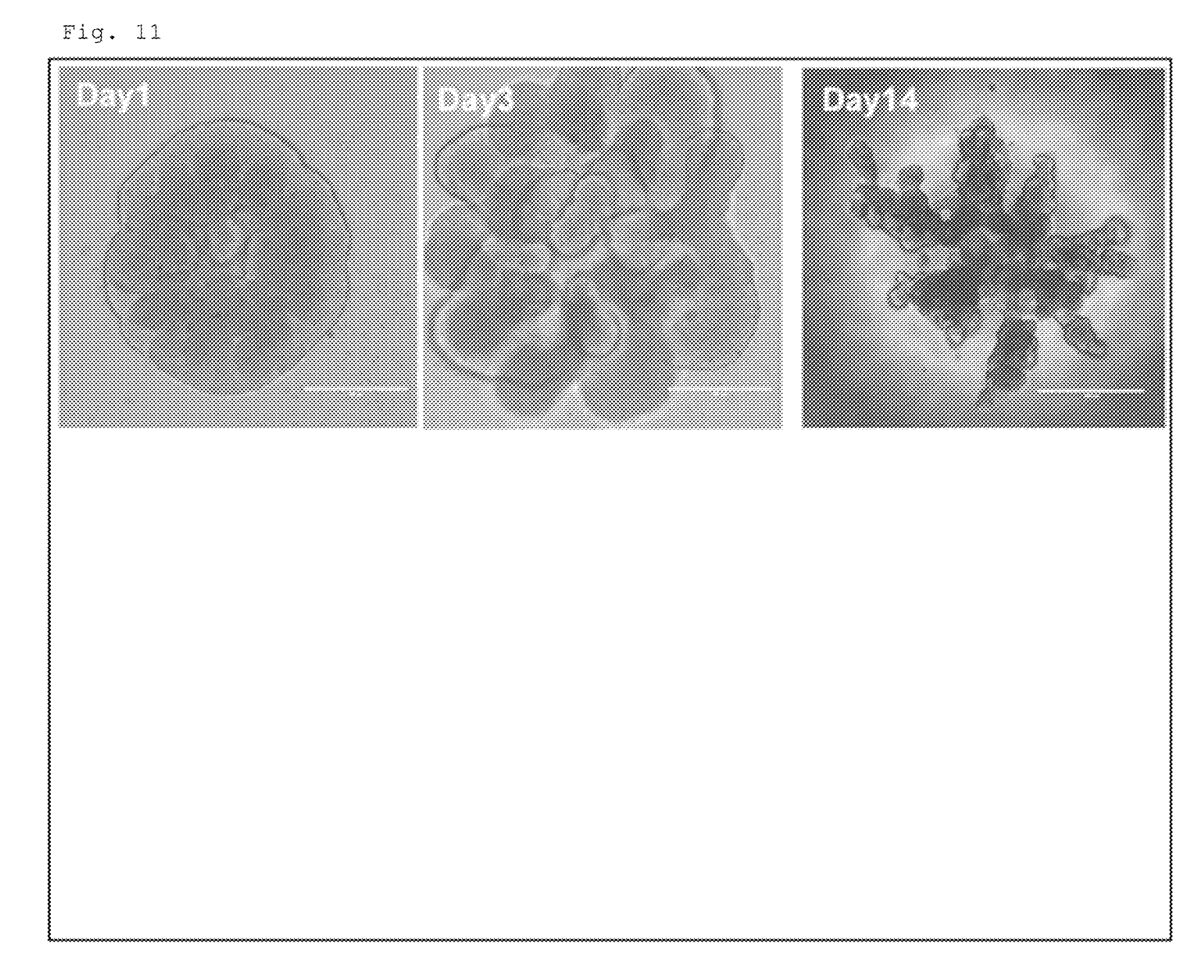
FIG. 11 shows an example of the process of ES cell-derived lacrimal gland organoid formation.

FIG. 11 shows that the ES cell-derived ocular surface stem cells also formed organoids having an adenoid structure.

INDUSTRIAL APPLICABILITY

The present invention provides a lacrimal gland organoid produced from pluripotent stem cells including iPS cells and thus is very useful for cell-based regenerative therapy for lacrimal gland-related diseases and cell-based research on the diseases.

The invention claimed is:

1. A method for producing a stem cell-derived lacrimal gland tissue, the method comprising:
    isolating SSEA4 and CD104 double positive cells from a self-formed ectodermal autonomous multi-zone (SEAM) cell population derived from pluripotent stem cells;
    culturing the isolated SSEA4 and CD104 double positive cells to form spheroids, and
    three-dimensionally culturing the spheroids in a medium comprising epidermal growth factor (EGF) and a ROCK inhibitor to produce a lacrimal gland tissue capable of expressing a lacrimal gland-related protein.

2. The method according to claim 1, wherein the isolated cells are negative for CD200.

3. A method for producing a stem cell-derived lacrimal gland tissue, the method comprising culturing limbal stem cells to form spheroids; and
    three-dimensionally culturing the spheroids in a medium comprising epidermal growth factor (EGF) and a ROCK inhibitor to produce lacrimal gland tissue capable of expressing a lacrimal gland-related protein.

4. The method according to claim 1, wherein the medium further comprises TGF-β.

5. The method according to claim 1, wherein the lacrimal gland-related protein is selected from AQP5, LYZ, CNN1, BARX2, SOX9, SOX10, RUNX1, TFCP2L1, LTF, or HTN1.

6. A method for producing a lacrimal gland organoid for transplantation, the method comprising producing a stem cell-derived lacrimal gland tissue by the method of claim 1 and culturing lacrimal gland epithelial cells obtained therefrom to produce the lacrimal gland organoid.

* * * * *